US008313934B2

(12) United States Patent
Bhatia et al.

(10) Patent No.: US 8,313,934 B2
(45) Date of Patent: Nov. 20, 2012

(54) REDUCTION OF THE TOXIC EFFECT OF IMPURITIES FROM RAW MATERIALS BY EXTRACTIVE FERMENTATION

(75) Inventors: Monica Bhatia, Sunnyvale, CA (US); Michael C. M. Cockrem, Madison, WI (US); Stephen B. del Cardayre, Belmont, CA (US); Fernando A. Sanchez-Riera, Eden Prairie, MN (US)

(73) Assignee: LS9, Inc., South San Francisco, CA (US)

( * ) Notice: Subject to any disclaimer, the term of this patent is extended or adjusted under 35 U.S.C. 154(b) by 509 days.

(21) Appl. No.: 12/239,562

(22) Filed: Sep. 26, 2008

(65) Prior Publication Data

US 2009/0084025 A1    Apr. 2, 2009

Related U.S. Application Data

(60) Provisional application No. 60/975,798, filed on Sep. 27, 2007.

(51) Int. Cl.
*C12P 7/62* (2006.01)

(52) U.S. Cl. ........ 435/135; 435/134; 435/148; 435/157; 435/167; 435/252.3; 435/252.33; 435/254.11

(58) Field of Classification Search ........................ None
See application file for complete search history.

(56) References Cited

U.S. PATENT DOCUMENTS

| | | | | |
|---|---|---|---|---|
| 5,158,887 | A * | 10/1992 | Hsu et al. | 435/252.7 |
| 6,750,048 | B2 | 6/2004 | Ruecker et al. | |
| 7,056,714 | B2 | 6/2006 | Rosazza et al. | |
| 7,425,433 | B2 | 9/2008 | Rosazza et al. | |
| 2004/0180400 | A1 | 9/2004 | Rosazza et al. | |
| 2006/0014977 | A1 | 1/2006 | Miller et al. | |
| 2006/0206963 | A1 | 9/2006 | Voelker et al. | |
| 2007/0192900 | A1 | 8/2007 | Stricklen | |
| 2007/0270319 | A1 | 11/2007 | Seggelkow et al. | |
| 2010/0199548 | A1 | 8/2010 | Del Cardayre et al. | |
| 2010/0242345 | A1 | 9/2010 | Keasling et al. | |
| 2010/0251601 | A1 | 10/2010 | Hu et al. | |
| 2011/0097769 | A1 | 4/2011 | Del Cardayre et al. | |

FOREIGN PATENT DOCUMENTS

| | | |
|---|---|---|
| WO | WO 2007/136762 A2 | 11/2007 |
| WO | WO 2008/100251 A1 | 8/2008 |
| WO | WO 2008/119082 A2 | 10/2008 |
| WO | WO 2009/009391 A2 | 1/2009 |

OTHER PUBLICATIONS

Campbell, J.W. et al, "The Enigmatic *Escherichia coli fadE* Gene is *yafH*", J. Bacteriology, vol. 184(13): 3759-3764 (2002).
Frazer, F.R. et al., "Wood Hydrolyzate Treatments for Improved Fermentation of Wood Sugars to 2,3-Butanediol", Biomass, vol. 18(1): 31-42 (1989).
Kalscheuer, R. et al., "Microdiesel: *Escherichia coli* engineered for fuel production", Microbiology, vol. 152(9): 2529-2536 (2006).

Mussatto, S.I., et al., "Alternatives for detoxification of diluted-acid lignocellulosic hydrolyzates for use in fermentative processes: a review", Bioresource Technology, vol. 93(1): 1-10 (2004).
Olsson, L. et al., "Fermentation of lignocellulosic hydrolysates for ethanol production" Enzyme Microb. Technol., vol. 18(5): 312-331 (1996).
Palmqvist, E. et al., "Fermentation of lignocellulosic hydrolysates. I: inhibition and detoxification", Bioresource Technology, vol. 74(1): 17-24 (2000).
Sahoo, P.K., et al., "Biodiesel development from high acid value potanga seed oil and performance evaluation in a CI engine", Fuel, vol. 86(3): 448-454 (2007).
Zaldivar, J. et al., "Effect of Selected Aldehydes on the Growth and Fermentation of Ethanologenic *Escherichia coli*", Biotech & Bioengineering, vol. 65(1): 24-33 (1999).
International Search Report and Written Opinion from PCT/US2008/077996, mailed Feb. 25, 2009.
Ahn, et al., "Production of Poly(3-Hydroxybutyrate) by Fed-Batch Culture of Recombinant *Escherichia coli* with a Highly Concentrated Whey Solution", Appln. Environ. Microbiol. 66(8): 3624-3627 (2000).
Alaeddinoglu et al., "Transfer of a Gene for Sucrose Utilization into *Escherichia coli* K12, and Consequent Failure of Expression of Genes for D-Serine Utilization", *J.Gen.Microbiol*. 110: 47-59 (1979).
Andersen et al., "Are Growth Rates of *Escherichia coli* in Batch Cultures Limited by Respiration?", *J.Bacteriol*. 144(1): 114-123 (1980).
Aristidou et al., "Metabolic Flux Analysis of *Escherichia coli* Expressing the *Bacillus subtilis* Acetolactate Synthase in Batch and Continuous Cultures", *Biotechnol.Bioeng*. 63(6): 737-749 (1999).
Arneborg, et al., "The effect of growth rate and other growth conditions on the lipid composition of *Escherichia coli*", *Appl.Microbiol.Biotechnol*. 39:353-357 (1993).
Aucoin et al., "Identifying conditions for inducible protein production in *E. coli*: combining a fed-batch and multiple induction approach", *Appl.Microbiol.Biotechnol*. 5:27 (2006).
Birge et al., "Acyl Carrier Protein. XVI.Intermediate Reactions of Unsaturated Fatty Acid Synthesis in *Escerichia Coli* and Studies of fab B Mutants", *J.Biol.Chem*. 247(16): 4921-4929 (1972).
Buist, P., "Catalytic diversity of fatty acid desaturases", *Tetrahedron: Asymmetry* 15: 2779-2785 (2004).
Chen et al., "Optimization of Fermentation Conditions for the Biosynthesis of L-Threonine by *Escherichia coli*", *Appl.Biochem. Biotechnol*. 158 (2009).
Dellomonaco et al., "Engineered Respiro-Fermentative Metabolism for the Production of Biofuels and Biochemicals from Fatty Acid-Rich Feedstocks", *Applied & Environmental Microbiology* 76(15): 5067-5078 (2010).
Dellomonaco et al., "The path to next generation biofuels: successes and challenges in the era of synthetic biology", *Microbial Cell Factories* 9(3): 1-15 (2010).

(Continued)

*Primary Examiner* — Jim Ketter

(74) *Attorney, Agent, or Firm* — Linda R. Judge; LS9 Inc.

(57) ABSTRACT

There are provided bioproducts and methods of improving production of the bioproducts from engineered microbial cells, the methods comprising: providing a fermentation broth comprising a crude carbon source; inoculating said fermentation broth with said microbial cells; and incubating the inoculated fermentation broth; wherein said bioproduct is a hydrophobic solvent immiscible with said fermentation broth, and wherein a toxic side product present in said crude carbon source is soluble in said hydrophobic solvent. Also, provided are kits for practicing the methods of improving production of bioproducts.

16 Claims, No Drawings

OTHER PUBLICATIONS

Desai et al., "Regulation of Arabinose and Xylose Metabolism in *Escherichia coli*", *Appl. Environ.Microbiol.* 76(5): 1524-1532 (2010).

Digman et al., "Recent Progress in Gasification/Pyrolysis Technologies for Biomass Conversion to Energy", *EPSE* 28(1): 47-51 (2009).

Duan et al., "De novo Biosynthesis of Biodiesel by *Escherichia coli* in Optimized Fed-Batch Cultivation", *PLoS ONE* 6(5): 1-7 (2011).

Franchini et al., "Global gene expression in *Escherichia coli* K-12 during short-term and long-term adaptation to glucose-limited continuous culture conditions", *Mircrobiol.* 152:2111-2127 (2006).

Frazer et al., "Wood Hydrolyzate Treatments for Improved Fermentation of Wood Sugars to 2,3-Butanediol", *Biomass* 18(1): 31-42 (1989).

Han et al., "Fed-Batch Cultivation of an Oxygen-Dependent Inducible Promoter System, the nar Promoter in *Escherichia coli* with an Inactivated nar Operon", *Biotech. & Bioengineering* 59(4): 400-406 (1998).

Hu et al., Microalgal triacylglycerols as feedstocks for biofuel production: perspectives and advances, *The Plant Journal* 54: 621-639 (2008).

Huber et al., "Production of Liquid Alkanes by Aqueous-Phase Processing of Biomass-Derived Carbohydrates", *Science* 308: 1446-1450 (2005).

Huber et al., "Synthesis of Transportation Fuels from Biomass: Chemistry, Catalysts, and Engineering", *Chem.Rev.106*: 1-55 (2006).

Jahreis et al., "Adaptation of Sucrose Metabolism in the *Escherichia coli* Wild-Type Strain EC3132", *J.Bacteriol.*184(19): 5307-5316 (2002).

Joshi et al., "Flow properties of biodiesel fuel blends at low temperatures", *Fuel* 86: 143-151 (2007).

Junker, B., "Scale-Up Methodologies for *Escherichia coli* and Yeast Fermentation Processes", *J.Biosci.Bioeng.* 97(6): 347-364 (2004).

Kaneshiro et al., "Conversion of Unsaturated Fatty Acids by Bacteria Isolated from Compost", *Curr.Microbiol.* 38:250-255 (1999).

Karakashev et al., "Anaerobic biotechnological approaches for production of liquid energy carriers from biomass", *Biotechnol.Lett.* 29: 1005-1012 (2007).

Kawaguchi et al., "Engineering of a Xylose Metabolic Pathway in *Corynebacterium glutamicum*" *Appl.Environ.Microbiol.* 72(5): 3418-3428 (2006).

Kawasaki et al., "Cloning and Expression in *Escherichia coli* of Sucrose Phosphorylase Gene from *Leuconostoc mesenteroides* No. 165", *Biosci. Biotech.Biochem.* 60 (2): 322 324 (1996).

Kayser et al., "Metabolic flux analysis of *Escherichia coli* in glucose-limited continuous culture. I. Growth-ratedependent metabolic efficiency at steady state", *Microbiol.*151: 693-706 (2005).

Kazan et al., "The Effect of Glucose Concentration on the Growth Rate and some Intracellular Components of a Recombinant *E. coli* Culture", Process Biochemistry 30(3): 269-273 (1995).

Keasling et al., "Metabolic engineering delivers next-generation biofuels", *Nature Biotechology* 26(3):298-299 (2008).

Kensy et al. "Scale-up from microtiter plate to laboratory fermenter: evaluation by online monitoring techniques of growth and protein expression in *Escherichia coli* and *Hansenula polymorpha* fermentations", *Microb.Cell.Fact.* 8:68: 1-15 (2009).

Koch et al., "Effect of Antifoam Agents on the Medium and Microbial Cell Properties and Process Performance in Small and Large Reactors", *Process Biochem.* 30(5): 435-446 (1995).

Kornberg et al., "Routes for Fructose Utilization by *Escherichia coli*", *J. Mol. Microbiol. Biotechnol.* 3(3): 355-359 (2001).

Lee et al., "Fed-batch culture of *Escherichia coli* W by exponential feeding of sucrose as a carbon source", *Biotech.Tech.* 11(1): 59-62 (1997).

Lemuth et al., "Global Transcription and Metabolic Flux Analysis of *Escherichia coli* in Glucose-Limited Fed-Batch Cultivations", *Appl. Environ. Micriobiol.* 74(22): 7002-7015 (2008).

Lendenmann et al., "Kinetics of the Simultaneous Utilization of Sugar Mixtures by *Escherichia coli* in Continuous Culture", *Appl. Environ. Microbiol.* 62(5): 1493-1499 (1996).

Lin et al., "Fed-Batch Culture of a Metabolically Engineered *Escherichia coli* Strain Designed for High-Level Succinate Production and Yield Under Aerobic Conditions", *Biotech.Engineering* 90: 1-5 (2005).

Lykidis et al., "Genomic Prospecting for Microbial Biodiesel Production," LBLN-301E, No. 10: 1-39 (2008).

Lynd et al., "Microbial Cellulose Utilization: Fundamentals and Biotechnology" *Microbiol.Mol.Biol.Rev.* 66(3): 506-577 (2002).

Marr, et al., "Effect of Temperature on the Composition of Fatty Acids in *Escherichia coli*", *J.Bacteriology* 84: 1260-1267 (1962).

Mayer et al., "Identification of amino acid residues involved in substrate specificity of plant acyl-ACP thioesterases using a bioinformatics-guided approach" *BMC Plant Biology* 7(1) (2001).

Morgan-Kiss et al, "The *Escherichia coli* fadK (ydiD) Gene Encodes an Anerobically Regulated Short Chain Acyl-CoA Synthetase," *J. Biol. Chem.*, 279(36): 37324-37333 (2004).

Morgan-Kiss et al., "The *Lactococcus lactis* FabF Fatty Acid Synthetic Enzyme can Functionally Replace both the FabB and FabF Proteins of *Escherichia coli* and the FabH Protein of *Lactococcus lacfis*," *Arch. Microbiol.* 190: 427-437 (2008).

Naccarato et al., "In Vivo and In Vitro Biosynthesis of Free Fatty Alcohols in *Escherichia coli* K-12," *Lipids*, 9(6): 419-428 (1973).

NCBI Reference Sequence GI:49532534, Putative Alcohol Dehydrogenase [*Acinetobacter* sp. ADP1] (2004).

Nunn et al., "Transport of long-chain fatty acids by *Escherichia coli*: Mapping and characterization of mutants in the *fadL* gene" *PNAS* 75(7): 3377-3381 (1978).

Nunn et al., "Role for fadR in Unsaturated Fatty Acid Biosynthesis in *Escherichia coli*", *J.Bacteriol.* 154(2):554-560 (1983).

Rafi et al., "Structure of Acyl Carrier Protein Bound to Fabl, the FASII Enoyl Reductase from *Escherichia Coli*" *J.Biol.Chem.* 281(51): 39285-39293 (2006).

Rawlings et al., "The Gene Encoding *Escherichia coli* Acyl Carrier Protein Lies within a Cluster of Fatty Acid Biosynthetic Genes", *J.Biol.Chem.* 267(9):5751-5754 (1992).

Rawlings et al., "Biosynthesis of fatty acids and related metabolites", *Natural Product Reports* 15: 275-308 (1998).

Ray et al., "Activation of long chain fatty acids with acyl carrier protein: Demonstration of a new enzyme, acyl-acyl carrier protein synthetase, in *Escherichia coli*" *PNAS* 73(12):4374-4378 (1976).

Regalbuto, J., "Cellulosic Biofuels—Got Gasoline?" *Science* 325: 822-824 (2009).

Reid et al., "Sucrose utilisation in bacteria: genetic organisation and regulation", *Appl Microbiol Biotechnol* 67: 312-321 (2005).

Ren et al., "FabG, an NADPH-Dependent 3-Ketoacyl Reductase of *Pseudomonas aeruginosa*, Provides Precursors for Medium-Chain-Length Poly-3-Hydroxyalkanoate Biosynthesis in *Escherichia coli*", *J. Bacteriol.*182(10):2978-2981 (2000).

Rock et al., "Acyl-Acyl Carrier Protein Synthetase from *Escherichia coli*" *Meth.Enzymol.* 71: 163-168 (1981).

Rude et al., "Terminal Olefin (1-Alkene) Biosynthesis by a Novel P450 Fatty Acid Decarboxylase from *Jeotgalicoccus* Species", *Appl. Environ.Microbiol.* 77(5): 1718-1727 (2011).

Rude et al., "New microbial fuels: a biotech perspective", *Current Opinion in Microbiology* 12: 274-281 (2009).

Schmid et al., "Plasmid-Mediated Uptake and Metabolism of Sucrose by *Escherichia coli* K-12", *J.Bacteriol.* 151(1): 68-76 (1982).

Schweizer et al., "Microbial Type I Fatty Acid Synthases (FAS): Major Players in a Network of Cellular FAS Systems", Microbiol. Mol.Biol.Rev. 68(3): 501-517 (2004).

Shockey et al., "Arabidopsis Contains Nine Long-Chain Acyl-Coenzyme A Synthetase Genes that Particpate in Fatty Acid and Glycerolipid Metabolism," *Plant Physiol.*, 129: 1710-1722 (2002).

Stafford et al., "Optimizing bioconversion pathways through systems analysis and metabolic engineering", PNAS 99(4): 1801-1806 (2002).

Steen et al., "Microbial production of fatty-acid-derived fuels and chemicals from plant biomass", *Nature* 463:559-563 (2010).

Trinh et al., "Design, construction and performance of the most efficient biomass producing *E. Coli* bacterium" *Metabolic Engineering* 8: 628-638 (2006).

Tsunekawa et al., "Acquisition of a sucrose utilization system in *Escherichia coli* K-12 derivatives and its application to industry", *Appln.Environ.Microbiol.* 58(6): 2081-2088 (1992).

Twaiq et al., "Performance of composite catalysts in palm oil cracking for the production of liquid fuels and chemicals", *Fuel Processing Technology*, 85: 1283-1300 (2004).

Vadali et al., "Cofactor engineering of intracellular CoA/acetyl-CoA and its effect on metabolic flux redistribution in *Escherichia coli*" *Metabolic Engineering* 6: 133-139 (2004).

Van Den Berg et al., "The FadL family: unusual transporters for unusual substrates", *Curr.Opin.Struct.Biol.* 15: 401-407 (2005).

Vanderhoeven et al., "Biosynthesis and Elongation of Short- and Medium-Chain-Length Fatty Acids", *Plant Physiology* 122: 275-282 (2000).

Voelker et al. "Alteration of the Specificity and Regulation of Fatty Acid Synthesis of *Escherichia coli* by Expression of a Plant Medium-Chain Acyl-Acyl Carrier Protein Thioesterase," *J. Bacteriol.*, 176(23): 7320-7327 (1994).

Wang et al., "Functional Replacement of the FabA and FabB Proteins of *Escherichia coli* Fatty Acid Synthesis by *Enterococcus faecalis* FabZ and FabF Homologues", *J.Biol.Chem.*279(33): 34489-34495 (2004).

White et al., "Carboxylic acid reductase: a new tungsten enzyme catalyzes the reduction of non-activated carboxylic acids to aldehydes", *Eur. J. Biochem.* 184: 89-96 (1989).

Xu et al., The FadRzDNA Complex. Transcriptional Control of Fatty Acid Metabolism in *Escherichia Coli*, *J.Biol.Chem*.276(20): 17373-17379 (2001).

Yoo et al., "Determination of the native form of FadD, the *Escherichia coli* fatty acyl-CoA synthetase, and characterization of limited proteolysis by outer membrane protease OmpT", *Biochem. J.* 360: 699-706 (2001).

Zhang, et al. "The FabR (YijC) Transcription Factor Regulates Unsaturated Fatty Acid Biosynthesis in *Escherichia coli*," *J. Biol. Chem.*, 277(18): 15558-15565 (2002).

Zhang et al., "Inhibiting Bacterial Fatty Acid Synthesis", *J.Biol. Chem.* 281(26): 17541-17544 (2006).

Zhang et al., "Structural Basis for Catalytic and Inhibitory Mechanisms of β-Hydroxyacyl-acyl Carrier Protein Dehydratase (FabZ)", *J.Biol.Chem.* 283(9):5370-5379 (2008).

Zhang, et al. "Molecular effect of FadD on the regulation and metabolism of fatty acid in *Escherichia coli*," *FEMS Microbiol. Lett.*, 259(2): 249-253 (2006).

Zheng et al., "Evaluation of Different Biomass Materials as Feedstock for Fermentable Sugar Production", *Appl.Biochem.Biotech.* 137-140: 423-436 (2007).

Zhu et al., "Functions of the *Clostridium acetobutylicium* FabF and FabZ proteins in unsaturated fatty acid biosynthesis", *BMC Microbiology* 9:119 (2009).

Zimhony et al., "Characterization of *Mycobacterium smegmatis* Expressing the *Mycobacterium tuberculosis* Fatty Acid Synthase I (*fas1*) Gene", *J.Bacteriology* 186(13): 4051-4055 (2004).

ISR and WO from PCT/US2007/003736, mailed Aug. 24, 2007.

\* cited by examiner

REDUCTION OF THE TOXIC EFFECT OF IMPURITIES FROM RAW MATERIALS BY EXTRACTIVE FERMENTATION

CROSS-REFERENCE TO RELATED APPLICATIONS

This patent application claims the benefit of U.S. Provisional Patent Application No. 60/975,798, filed Sep. 27, 2007, which are incorporated by reference.

BACKGROUND

Petroleum is a limited, natural resource found in the earth in liquid, gaseous, or solid forms. Petroleum is primarily composed of hydrocarbons, which are comprised mainly of carbon and hydrogen. It also contains significant amounts of other elements, such as, nitrogen, oxygen, or sulfur, in different forms. In addition to the problems with exploring, extracting, transporting, and refining petroleum, petroleum is a limited and dwindling resource. One estimate of world petroleum consumption is 30 billion barrels per year. By some estimates, it is predicted that at current production levels, the world's petroleum reserves could be depleted before the year 2050.

Petroleum is a valuable resource, but petroleum products are developed at considerable costs, both financial and environmental. First, sources of petroleum must be discovered. Petroleum exploration is an expensive and risky venture. The cost of exploring deep water wells can exceed $100 million. Moreover, there is no guarantee that these wells will contain petroleum. It is estimated that only 40% of drilled wells lead to productive wells generating commercial hydrocarbons. Petroleum extraction also carries an environmental cost. For example, petroleum extraction can result in large seepages of petroleum rising to the surface. Moreover, offshore drilling involves dredging the seabed which disrupts or destroys the surrounding marine environment.

After a productive well is discovered. the petroleum must be extracted from the earth at great expense. During primary recovery, the natural pressure underground is sufficient to extract about 20% of the petroleum in the well. As this natural pressure falls, secondary recovery methods are employed. Generally, secondary recovery involves increasing the well's pressure by, for example, water injection, natural gas injection, or gas lift. Using secondary recovery methods, an additional 5% to 15% of petroleum is recovered. Once secondary recovery methods are exhausted, tertiary recovery methods can be used. Tertiary methods involve reducing the viscosity of the petroleum to make it easier to extract. Using tertiary recovery methods, an additional 5% to 15% of petroleum is recovered. Hence, even under the best circumstances, only 50% of the petroleum in a well can be extracted.

Since petroleum deposits are not found uniformly throughout the earth, petroleum must be transported over great distances from petroleum producing regions to petroleum consuming regions. In addition to the shipping costs, there is also the environmental risk of devastating oil spills.

In its natural form, crude petroleum extracted from the earth has few commercial uses. It is a mixture of hydrocarbons (e.g., paraffins (or alkanes), olefins (or alkenes), alkynes, napthenes (or cycloalkanes), aliphatic compounds, aromatic compounds, etc.) of varying length and complexity. In addition, crude petroleum contains other organic compounds (e.g., organic compounds containing nitrogen, oxygen, sulfur, etc.) and impurities (e.g., sulfur, salt, acid, metals, etc.).

Hence, crude petroleum must be refined and purified before it can be used commercially. Due to its high energy density and its easy transportability, most petroleum is refined into fuels, such as transportation fuels (e.g., gasoline, diesel, aviation fuel, etc.), heating oil, liquefied petroleum gas, etc.

Crude petroleum is also a primary source of raw materials for producing petrochemicals. The two main classes of raw materials derived from petroleum are short chain olefins (e.g., ethylene and propylene) and aromatics (e.g., benzene and xylene isomers). These raw materials are derived from longer chain hydrocarbons in crude petroleum by cracking it at considerable expense using a variety of methods, such as catalytic cracking, steam cracking, or catalytic reforming. These raw materials are used to make petrochemicals, which cannot be directly refined from crude petroleum, such as monomers, solvents, detergents, or adhesives.

One example of a raw material derived from crude petroleum is ethylene. Ethylene is used to produce petrochemicals such as, polyethylene, ethanol, ethylene oxide, ethylene glycol, polyester, glycol ether, ethoxylate, vinyl acetate, 1,2-dichloroethane, trichloroethylene, tetrachloroethylene, vinyl chloride, and polyvinyl chloride. An additional example of a raw material is propylene, which is used to produce isopropyl alcohol, acrylonitrile, polypropylene, propylene oxide, propylene glycol, glycol ethers, butylene, isobutylene, 1,3-butadiene, synthetic elastomers, polyolefins, alpha-olefins, fatty alcohols, acrylic acid, acrylic polymers, allyl chloride, epichlorohydrin, and epoxy resins.

These petrochemicals can then be used to make specialty chemicals, such as plastics, resins, fibers, elastomers, pharmaceuticals, lubricants, or gels. Particular specialty chemicals which can be produced from petrochemical raw materials are: fatty acids, hydrocarbons (e.g., long chain, branched chain, saturated, unsaturated, etc.), fatty alcohols, esters, fatty aldehydes, ketones, lubricants, etc.

Specialty chemicals have many commercial uses. Fatty acids are used commercially as surfactants, for example, in detergents and soaps. They can also be used as additives in fuels, lubricating oils, paints, lacquers, candles, salad oil, shortening, cosmetics, and emulsifiers. In addition, fatty acids are used as accelerator activators in rubber products. Fatty acids can also be used as a feedstock to produce methyl esters, amides, amines, acid chlorides, anhydrides, ketene dimers, and peroxy acids and esters.

Hydrocarbons have many commercial uses. For example, shorter chain alkanes are used as fuels. Methane and ethane are the main constituents of natural gas. Longer chain alkanes (e.g., from five to sixteen carbons) are used as transportation fuels (e.g., gasoline, diesel, or aviation fuel). Alkanes having more than sixteen carbon atoms are important components of fuel oils and lubricating oils. Even longer alkanes, which are solid at room temperature, can be used, for example, as a paraffin wax. Alkanes that contain approximately thirty-five carbons are found in bitumen, which is used for road surfacing. In addition, longer chain alkanes can be cracked to produce commercially useful shorter chain hydrocarbons.

Like short chain alkanes, short chain alkenes are used in transportation fuels. Longer chain alkenes are used in plastics, lubricants, and synthetic lubricants. In addition, alkenes are used as a feedstock to produce alcohols, esters, plasticizers, surfactants, tertiary amines, enhanced oil recovery agents, fatty acids, thiols, alkenylsuccinic anhydrides, epoxides, chlorinated alkanes, chlorinated alkenes, waxes, fuel additives, and drag flow reducers.

Fatty alcohols have many commercial uses, including for example, the use of shorter chain fatty alcohols are used in the cosmetic and food industries as emulsifiers, emollients, and thickeners. Due to their amphiphilic nature, fatty alcohols behave as nonionic surfactants, which are useful as detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats.

Esters have many commercial uses, including for example, biodiesel as an alternative fuel. Biodiesel is comprised of esters (e.g., fatty acid methyl ester, fatty acid ethyl esters, etc.). Some low molecular weight esters are volatile with a pleasant odor which makes them useful as fragrances or flavoring agents. In addition, esters are used as solvents for lacquers, paints, and varnishes. Furthermore, some naturally occurring substances, such as waxes, fats, and oils are comprised of esters. Esters are also used as softening agents in resins and plastics, plasticizers, flame retardants, and additives in gasoline and oil. In addition, esters can be used in the manufacture of polymers, films, textiles, dyes, and pharmaceuticals.

Aldehydes are used to produce many specialty chemicals, including for example, production of polymers, resins (e.g., Bakelite), dyes, flavorings, plasticizers, perfumes, pharmaceuticals, and other chemicals. Some are used as solvents, preservatives, or disinfectants. Some natural and synthetic compounds, such as vitamins and hormones, are aldehydes. In addition, many sugars contain aldehyde groups.

Ketones are used commercially as solvents. For example, acetone is frequently used as a solvent, but it is also a raw material for making polymers. Ketones are also used in lacquers, paints, explosives, perfumes, and textile processing. In addition, ketones are used to produce alcohols, alkenes, alkanes, imines, and enamines.

In addition, crude petroleum is a source of lubricants. Lubricants derived from petroleum are typically composed of olefins, particularly polyolefins and alpha-olefins. Lubricants can either be refined from crude petroleum or manufactured using raw materials refined from crude petroleum.

Obtaining these specialty chemicals from crude petroleum requires a significant financial investment as well as a great deal of energy. It is also an inefficient process because frequently the long chain hydrocarbons in crude petroleum are cracked to produce smaller monomers. These monomers are then used as the raw material to manufacture the more complex specialty chemicals.

Finally, the burning of petroleum based fuels releases greenhouse gases (e.g., carbon dioxide) and other forms of air pollution (e.g., carbon monoxide, sulfur dioxide, etc.). As the world's demand for fuel increases, the emission of greenhouse gases and other forms of air pollution also increases. The accumulation of greenhouse gases in the atmosphere leads to an increase in global warming. Hence, in addition to damaging the environment locally (e.g., oil spills, dredging of marine environments, etc.), burning petroleum also damages the environment globally.

Due to the inherent challenges posed by petroleum, there is a need for a renewable petroleum source that avoids the cost, time and energy involved in exploration, extraction, transportation over long distances, and refining of petroleum. There is also a need for a renewable petroleum source which can be produced economically without creating environmental damage produced by the petroleum industry and the burning of petroleum based fuels. For similar reasons, there is also a need for a renewable source of chemicals which are typically derived from petroleum.

One method of producing renewable petroleum is by engineering microorganisms to produce renewable petroleum products. Some microorganisms have a natural ability to produce chemicals. For example, yeast has been used for centuries to produce ethanol (e.g., beer, wine, etc.). In recent years, through the development of advanced biotechnologies, it is possible to metabolically engineer an organism to produce bioproducts not normally produced by the organism (or produced at substantially lower levels). Products, such as chemicals, derived from these cellular activities are known as bioproducts. Fuels produced by these cellular activities are known as biofuels. Biofuels are a renewable alternative to petroleum based fuels. Biofuels can be substituted for any petroleum based fuel (e.g., gasoline, diesel, aviation fuel, heating oil, etc.). Biofuels can be derived from renewable sources, such as plant matter, animal matter, or even waste products. These renewable sources are collectively known as biomass. One advantage of biofuels over petroleum based fuels is that they do not require expensive and risky exploration or extraction. In addition, biofuels can be locally produced. Hence, they do not require transportation over long distances. Moreover, biofuels can be made directly without the need for expensive and energy intensive refining as is needed with refining crude petroleum, or it may require a limited and cost-effective level of refining. Furthermore, the use of biofuels improves the environment by reducing the amount of environmentally harmful emissions (e.g., green house gases, air pollution, etc.) released during combustion of petroleum based fuels. Since the amount of carbon emitted by burning biofuels is equal to the amount of carbon utilized in their production from biomass, biofuels are considered to be carbon neutral. For example, biofuels maintain a balanced carbon cycle because biofuels are produced from biomass, a renewable, natural resource. While the burning of biofuels will release carbon (e.g., as carbon dioxide), this carbon will be recycled during the production of biomass (e.g., the cultivation of crops) thereby balancing the carbon cycle unlike petroleum based fuels.

For similar reasons, biologically derived chemicals offer the same advantages as biofuels over petroleum based fuels. Biologically derived chemicals are a renewable alternative to petrochemicals. Biologically derived chemicals, such as hydrocarbons (e.g., alkanes, alkenes, or alkynes), fatty alcohols, esters, fatty acids, fatty aldehydes, and ketones are superior to petrochemicals because they are produced directly without extensive refining. Unlike petrochemicals, biologically derived chemicals do not need to be refined like crude petroleum to recover raw materials which must then be further processed to make more complex petrochemicals. Biologically derived chemicals are directly converted from biomass to the desired chemical product.

Prior to bioconversion by the cells to result in the desired bioproduct, the biomass can be treated to convert the biomass into a soluble carbon source, or crude carbon source (e.g., carbohydrates, sugars, glucose, etc.). The conversion of biomass into a crude carbon source involves using, for example, enzymes, dilute mineral acids or bases, such as lime solution. Such treatment can also involve, for example, a thermal processing step during which the temperature is increased. A common side effect of these treatments is the generation of side products that are often toxic or inhibitory to the cells. For example, during hydrolysis of lignocellulosic materials complex mixtures of side products that are inhibitory to the cells are generated. These compounds can be divided into three major groups: weak acids (e.g., acetic, formic, etc.), furan derivatives (e.g., furfural, hydromethylfurfural, etc.), and phenolic compounds. These side products adversely affect the growth of microorganisms, and therefore reduce the overall efficiency of converting the carbon source to commercially valuable compounds. Also, the need to remove or dilute these unwanted toxins leads to substantial increases in the final product cost.

Therefore, there is a need for a process for producing commercially valuable bioproducts, such as biofuels, from an engineered microbe using a crude carbon source, where the crude carbon source contains side products inhibitory to cellular bioconversion. In particular, the needed processes are those that are efficient and economical at large scale.

SUMMARY OF INVENTION

An aspect of the invention comprises methods of improving production of a bioproduct from engineered microbial cells, comprising providing a fermentation broth comprising a crude carbon source; inoculating said fermentation broth with said microbial cells; and incubating the inoculated fermentation broth; wherein said bioproduct is a hydrophobic solvent immiscible with said fermentation broth, and wherein a toxic side product present in said crude carbon source is soluble in said hydrophobic solvent.

Another aspect of the invention comprises methods of passively phase-separating a toxic side product from an aqueous phase of a fermentation broth that is a mixture of crude carbon source and microbial cells engineered to produce a bioproduct during fermentation of a culture of said microbial cells, comprising: providing a fermentation broth comprising a crude carbon source; inoculating said fermentation broth with said microbial cells to form a fermentation culture; and incubating said fermentation culture to yield production of said bioproduct; wherein said bioproduct is a hydrophobic solvent, and wherein a toxic side product present in said crude carbon source is soluble in said hydrophobic solvent.

Another aspect of the invention comprises kits for producing bioproducts from bioengineered cells, comprising: a sample of bioengineered cells that are bioengineered to produce a bioproduct from a carbon source; a fermentation broth comprising a crude carbon source derived from conversion of a biomass; a hydrophobic solvent immiscible with said fermentation broth and capable of extracting a toxic side product formed during conversion of said biomass; and instructions for a fermentation process using said sample of bioengineered cells, fermentation broth, and hydrophobic solvent.

Still another aspect of the invention comprises continuous fermentation processes for the production of a bioproduct from engineered microbial cells, comprising: providing a culture of said microbial cells; introducing a continuous flow of volume of a fermentation broth comprising a crude carbon source to said culture; fermenting said culture with said fermentation broth; and removing a continuous flow of volume of said fermentation broth from said culture; wherein said bioproduct is a hydrophobic solvent that is immiscible with said fermentation broth, and wherein a toxic side product present in said crude carbon source is soluble in said hydrophobic solvent.

In still another aspect of the invention, provided are bioproducts produced by an engineered microbial cell by a process comprising: preparing a fermentation broth comprising a crude carbon source; inoculating said fermentation broth with said microbial cells; incubating the inoculated fermentation broth; recovering said bioproduct from the incubated fermentation broth; wherein said bioproduct is a hydrophobic solvent immiscible with said fermentation broth, and wherein a toxic side product present in said crude carbon source is soluble in said hydrophobic solvent.

In yet another aspect of the invention, provided are vehicles powered by energy from combustion of a bioproduct produced by an engineered microbial cell by a process comprising: preparing a fermentation broth comprising a crude carbon source; inoculating said fermentation broth with said microbial cells; incubating the inoculated fermentation broth; recovering said bioproduct from the incubated fermentation broth; wherein said bioproduct is a hydrophobic solvent immiscible with said fermentation broth, and wherein a toxic side product present in said crude carbon source is soluble in said hydrophobic solvent.

DETAILED DESCRIPTION OF PREFERRED EMBODIMENTS

"Bioconversion" and "fermentation" are used interchangeably herein. Fermentation is a chemical change induced by a living organism (e.g., bacteria, unicellular plants, such as yeast, molds, or fungi) or enzyme. The reaction can involve the conversion of a carbon source (e.g., sugar, starch, carbohydrate, etc.) into a bioproduct. As used herein, the reaction can occur under anaerobic, microaerobic, or aerobic conditions.

The term "biodiesel" is used herein to mean a particular type of biofuel. Biodiesel can be a substitute of diesel, which is derived from petroleum. Biodiesel can be used in internal combustion diesel engines in either a pure form, which is referred to as "neat" biodiesel, or as a mixture in any concentration with petroleum-based diesel. Biodiesel can be comprised of hydrocarbons or esters. In one embodiment, biodiesel is comprised of fatty esters, such as fatty acid methyl esters (FAME) or fatty acid ethyl esters (FAEE). In a preferred embodiment, these FAME and FAEE are comprised of fatty acyl moieties having a carbon chain length of about 8-20, 10-18, or 12-16 carbons in length. Fatty esters used as biodiesel may contain carbon chains which are saturated or unsaturated.

The term "biofuel" is used herein to mean a combustible fuel made of long chain hydrocarbons or esters, preferably ones that are biodegradable, and more preferably ones that are clean-burning combustibles. The term biofuel also includes biodiesel.

As used herein, the term "biomass" refers to any biological material from which a carbon source is derived. The carbon source can then be converted by the engineered microbial cell discussed herein to a synthetic bioproduct, including in some instances a biofuel. Biomass can include waste products from industry, agriculture, forestry, or households. Examples of such waste products that can be used as biomass are fermentation waste, straw, lumber, sewage, garbage, and food leftovers. Biomass also includes sources of carbon, such as carbohydrates (e.g., monosaccharides, disaccharides, or polysaccharides). Preferably the biomass used with the provided methods are those that require some initial processing before being used in a bioconversion to a bioproduct. The processing of biomass can result in the formation of toxic chemicals. Examples of such toxic chemicals, or toxic side products, include furfural, 5-hydroxymethyl furfural, aliphatic acids, phenolic compounds, 4-hydroxybenzaldehyde, 4-hydroxybenzoic acid, hydroquinone, catechol, 4-methyl catechol, syringaldehyde, syringic acid, guaiacol, vanillic acid, or vanillin.

The term "bioproduct" is used herein to mean an organic molecule produced by an engineered microbial cell (e.g., an *E. coli* cell). Preferably, the engineered microbial cell has been engineered to produce said bioproduct. The bioproduct can be almost any organic molecule that can be produced by the metabolic machinery of the engineered microbial cell and is preferably an organic molecule which can be used as an industrial product, a starting reagent for an industrial product, or a biofuel. For example, a bioproduct can include alkanes, esters, olefins (e.g., internal olefins, terminal olefins, etc.), fatty acids, fatty alcohols, aldehydes, or ketones.

As used herein, the phrase "carbon source" refers to a substrate or compound suitable to be used as a source of carbon for supporting prokaryotic or simple eukaryotic cell growth.

Carbon sources can be in various forms, including, but not limited to polymers, carbohydrates, acids, alcohols, aldehydes, ketones, amino acids, peptides, and gases (e.g., CO and $CO_2$). These include, for example, various monosaccharides, such as glucose, fructose, mannose, galactose, xylose, and arabinose; oligosaccharides, such as fructo-oligosaccharide and galacto-oligosaccharide; disaccharides, such as sucrose, maltose, and turanose; cellulosic material, such as methyl cellulose and sodium carboxymethyl cellulose; lignocellulosic material; hemicellulosic material; organic acids, such as succinate, lactate, and acetate; alcohols, such as ethanol; or mixtures thereof.

The carbon source can also be a product of photosynthesis, including, but not limited to, glucose.

Preferably, a carbon source is one that is ultimately derived from a processed or treated biomass. For example, the biomass can be treated to produce a monosaccharide, such as glucose; a polysaccharide, such as a starch; or, a disaccharide derived, for example, from sugar beets or molasses. A preferred carbon source is glucose.

After treatment of the biomass, the carbon source is in a crude state and generally requires purification to achieve a purity level for efficient utilization by the engineered microbial cells.

The phrase "conversion of biomass" or "treatment of biomass" used herein refers to treatment or conversion of biomass to yield a soluble carbon source, or crude carbon source (e.g., carbohydrates, sugars, etc.). The converting of biomass into a crude carbon source involves using, for example, enzymes, dilute mineral acids or bases, such as lime solution. Such treatment can also involve, for example, a thermal processing step during which the temperature is increased. A common side effect, however, of these treatments is the generation of side products that are often toxic or inhibitory to the cells.

A "crude carbon source" is used herein to mean a carbon source that is in a raw state or a process state where the carbon source is impure and includes, among other chemicals, the presence of toxic chemicals or toxic side products that can be inhibitory to cell growth or cell function. The crude carbon source is derived from biomass. The processing of biomass to the crude carbon source can result in the formation of toxic chemicals including, for example, furfural, 5-hydroxymethyl furfural, aliphatic acids, phenolic compounds, 4-hydroxybenzaldehyde, 4-hydroxybenzoic acid, hydroquinone, catechol, 4-methyl catechol, syringaldehyde, syringic acid, guaiacol, vanillic acid, or vanillin.

An "engineered microbial cell" is used herein to mean a microbe or microbial cell that has been metabolically engineered, for example, by modifying the microbial cell by transfection or transformation with a nucleic acid sequence, which is preferably a heterologous sequence. The microbial cell is also referred to as a production host (i.e., a microbial host metabolically engineered for the production of bioproducts).

"Fermentation broth" or "bioconversion broth" is used herein interchangeably to mean a broth or aqueous mixture of chemicals or materials used to support microbial cells, and typically includes a crude carbon source, a nitrogen source (e.g., ammonium salt, yeast extract or peptone), minerals, salts, cofactors, buffers, and other components known to those skilled in the art. The fermentation broth also provides the engineered microbial cells described herein with the starting reagents necessary for the cells to produce the desired bioproduct.

The term "hydrophobic solvent" is used herein to mean an organic compound in liquid phase, or alternatively a mixture of organic compounds in liquid phase that has hydrophobic properties, wherein such hydrophobic properties cause the hydrophobic solvent to be immiscible in a fermentation broth. The hydrophobic solvent can be used with the methods described below, and preferably is a hydrophobic solvent used to pretreat a crude carbon source, such as a processed biomass, to remove toxic side products. In a preferred embodiment, the bioproduct is a hydrophobic solvent, although the bioproduct is generally referred to as the desired bioproduct produced by the engineered microbial cell and not the solvent used for treating the crude carbon source. In other embodiments, the hydrophobic solvent used to treat the crude carbon source can be the same compound as the bioproduct produced.

The term "immiscible" is used herein to describe substances of the same phase or state of matter that are unable to uniformly mix or blend together, and preferably means the separation between the aqueous phase of the fermentation broth and the organic phase of the hydrophobic solvent (and/or the bioproduct). In addition, immiscible may also refer to substances of the same phase or state of matter that are not completely immiscible (i.e., partially miscible).

The terms "toxins," "toxic products," or "toxic side products" are used interchangeably when referring to the methods provided herein and mean a side product produced during the processing of a biomass to a carbon source useable by microbial cells. For example, during hydrolysis of lignocellulosic materials, three major groups of toxic side products are formed: weak acids (e.g., acetic acid, formic acid), furan derivatives (e.g., furfural and hydromethylfurfural), and phenolic compounds.

Engineered Microbial Cells

A variety of engineered microbial cells can be used with the processes and kits discussed herein. The strain of cells chosen for bioconversion, preferably large-scale bioconversion, to produce the biosynthetic products, preferably biofuels, will be based upon the crude carbon source utilized, as some crude carbon sources include certain toxic side products, and the solvent utilized (to phase partition away the same toxins from the fermentation broth).

The disclosure in PCT publication WO 2007/136762 A2 ("WO '762 pub") is hereby incorporated by reference in its entirety. In particular, the engineered microbial cells discussed in the WO '762 pub are incorporated herein, including microorganisms that produce fatty acid derivatives having defined carbon chain length, branching, and saturation levels.

In some examples, microorganisms have been engineered to include one or more exogenous nucleic acid sequences encoding a thioesterase (EC 3.1.2.14), ester synthase (EC 2.3.1.75), alcohol acetyltransferase (2.3.1.84), acyl-CoA reductase (EC 1.2.1.50), alcohol dehydrogenase (EC 1.1.1.1), a fatty alcohol forming acyl-CoA reductase (1.1.1.*), or other fatty acid (or derivatives thereof) metabolizing enzymes available in the art. The thioesterase peptides encoded by the exogenous nucleic acid sequences can be chosen to provide homogeneous products.

In some embodiments, the cell which can be engineered is selected from the group consisting of a mammalian cell, plant cell, insect cell, yeast cell, fungus cell, filamentous fungi cell, and bacterial cell.

In some embodiments, the engineered microbial cell is a Gram positive bacterial cell. In other embodiments, the host cell is a Gram negative bacterial cell.

In some embodiments, the microbial cell which can be engineered is selected from the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia*, or *Streptomyces*.

In particular embodiments, the microbial cell which can be engineered is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In other embodiments, the engineered microbial cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell.

In yet other embodiments, the engineered microbial cell is a *Streptomyces lividans* cell or a *Streptomyces murinus* cell. In other embodiments, the host cell is an *Actinomycetes* cell.

In some embodiments, the microbial cell which can be engineered is a CHO cell, a COS cell, a VERO cell, a BHK cell, a HeLa cell, a Cv1 cell, an MDCK cell, a 293 cell, a 3T3 cell, or a PC12 cell.

In particular embodiments, the engineered microbial cell is an *E. coli* cell, such as a strain B, a strain C, a strain K, or a strain W *E. coli* cell In some examples the microorganism that is engineered to produce the bioproduct is, *Z. mobilis, Ralstonia eutropha, Vibrio furnissii, Saccharomyces cerevisiae, Lactococcus lactis, Stenotrophomonas maltophila*, or *Micrococus leuteus* and their relatives.

In some examples, microorganisms that produce bioproducts endogenously can be engineered to overproduce bioproducts by optimizing the fatty acid biosynthetic pathway as described herein. Exemplary microorganisms that are known to produce bioproducts, and can be engineered to over-produce organic compounds or bioproducts using the teachings provided herein include *Arthrobacter* sp., *Botryococcus braunii, Chromatium* sp., *Cladosporium resina* (ATCC2271 1), *Clostridium pasteurianum* VKM, *Clostridium tenanomorphum, Clostridium acidiurici, Corynebacterium* species, cyanobacterial species (*Nostoc muscorum, Anacystis*(*Synechococcus*) *nidulans, Phormidium luridum, Chlorogloeafritschii, Trichodesmium erythaeum, Oscillatoria williamsii, Microcoleus chthonoplaseis, Coccochloris elabens, Agmenellum quadruplicatum, Plectonema terebrans, M. vaginatus*, and *C. scopulorum*), *Desulfovibrio desulfinuricans* (ATCC29577), *Kineococcus radiotolerans* (BAA-149), *Micrococcus luteus* (FD533, ATCC 272, 381, 382, 1SD, 540, 4698, 7468, 27141), *Micrococcus* sp. (ATCC 146, 398, 401, 533), *Micrococcus roseus* (ATCC 412, 416, 516), *Micrococcus lysodeikticus, Mycobacterium* species, *Trichoderma virida, Pullularia pullulans, Jeotgalicoccus* sp. (*M. candicans*)(ATCC 8456). *Rhodopseudomonas spheroids, Chlorobium* sp., *Rhodospirillium rubrum* (ATCCl1170). *Rhodomicrobium vannielii, Stenotrophomonas maltophilia* (ATCC 13637, 17444, 17445, 17666, 11668, 17673, 17674, 17679, 17617). *Saccharomycodes ludwigii* (ATCC 22111). *Saccharomyces* sp. (*oviformus, ludwiggi. tropicalis*), *Vibrio furnissii* Ml, *Vibrio marinus* MP-1, *Vibrio ponticus. Serratia marinorubra, Ustilago maydis, Ustilago nuda, Urocystis agropyri, Sphacelotheca reiliana, Tilletfa* sp. (*foetida, caries, controversa*), *Candida lipolytica, E. coli Arthrobacter* AK 19, *Rhodotorula glutinins, Acinetobacter* sp. strain M-1, and *Candida lipolytica*.

In addition to being engineered to express exogenous nucleic acid sequences that allow for the production of bioproducts, such as fatty acid derivatives, the microorganism can additionally have one or more endogenous genes functionally deleted or attenuated. For example, ackA (EC 2.7.2.1), ackB (EC 2.7.2.1), adhE (EC 1.1.1.1, 1.2.1.10), fabF (Ee 2.3.1.119), fabR (accession NP_18398), fadE (Ee 1.3.99.3, 1.3.99.-), GST (EC 6.3.2.3), gpsA (EC 1.1.1.94), ldhA (EC 1.1.1.28), pflB (EC 2.3.1.54), plsB (EC 2.3.1.15), poxB (EC 1.2.2.2), pta (BC 2.3.1.8), glutathione synthase (EC 6.3.2.3) and combinations thereof can be attenuated.

In addition, the microorganism can additionally have one or more additional genes overexpressed. For example, pdh, panK, aceEF (encoding the E1p dehydrogenase component and the E2p dihydrolipoamide acyltransferase component of the pyruvate and 2-oxoglutarate dehydrogenase complexes, Accessions: NP_414656, NP_414657, EC: 1.2.4.1, 2.3.1.61, 2.3.1.12), accABCD/fabH/fabD/fabG/acpP/fabF (encoding FAS, Accessions: CAD85557, CAD85558, NP_842277, NP_841683. NP_415613, EC: 2.3.1.180, 2.3.1.39, 1.1.1.100, 1.6.5.3, 2.3.1.179), genes encoding fatty-acyl-coA reductases (Accessions: AAC45217, EC 1.2.1.-), UdhA or similar genes (encoding pyridine nucleotide transhydrogenase, Accession: CAA46822, EC: 1.6.1.1) and genes encoding fatty-acyl-coA reductases (Accessions: AAC45211, EC 1.2.1.-).

Preferably, the engineered microbial cells are production hosts or microbes that include a nucleic acid sequence modified to overexpress the gene encoding an acyl-CoA synthase, a thioesterase, or an ester synthase. In some examples, the nucleic acid sequence is modified to overexpress the genes encoding an acyl-CoA synthase and a thioesterase or an ester synthase. In some examples, the nucleic acid sequence is modified to overexpress the gene encoding an acyl-CoA synthase, a thioesterase, and an ester synthase. In some examples, the nucleic acid sequence further comprises a nucleic acid sequence encoding an acyl-CoA dehydrogenase which is modified such that expression of the acyl-CoA dehydrogenase is attenuated.

The chain length of a fatty acid derivative substrate can be selected for by modifying the expression of selected thioesterases. Thioesterase influences the chain length of fatty acids produced. Hence, host cells can be engineered to express, overexpress, have attenuated expression, or not to express one or more selected thioesterases to increase the production of a preferred fatty acid derivative substrate. For example, $C_{10}$ fatty acids can be produced by expressing a thioesterase that has a preference for producing $C_{10}$ fatty acids and attenuating thioesterases that have a preference for producing fatty acids other than $C_{10}$ fatty acids (e.g., a thioesterase which prefers to produce $C_{14}$ fatty acids). This would result in a relatively homogeneous population of fatty acids that have a carbon chain length of 10. In other instances, $C_{14}$ fatty acids can be produced by attenuating endogenous thioesterases that produce non-$C_{14}$ fatty acids and expressing the thioesterases that use $C_{14}$-ACP. In some situations, $C_{12}$ fatty acids can be produced by expressing thioesterases that use $C_{12}$-ACP and attenuating thioesterases that produce non- $C_{12}$ fatty acids. Acetyl-CoA, malonyl-CoA, and fatty acid overproduction can be verified using methods known in the art, for example, by using radioactive precursors, HPLC, or GC-MS subsequent to cell lysis. Non-limiting examples of thioesterases that can be used in the methods described herein are listed in Table 1.

verted to acyl-CoA. One method of making fatty acid derivatives involves increasing the expression of, or expressing more active forms of, one or more acyl-CoA synthase peptides (EC 6.2.1.-). A list of acyl-CoA synthases that can be expressed to produce acyl-CoA and fatty acid derivatives is shown in Table B.

TABLE B

Acyl-CoA synthases

| Gene Name/Locus | Source | NCBI ID | % Identity to E. coli FadD | % Similarity to E. coli FadD |
|---|---|---|---|---|
| fadD | E. coli | NP_416319 | — | — |
| fadK | E. coli | YP_416216 | 45 | 27 |
| fadD | Acinetobacter sp. ADP1 | YP_045024 | 51 | 70 |
| fadD | Haemophilus influenza RdKW20 | NP_438551 | 64 | 78 |
| BH3103 | Bacillus halodurans C-125 | NP_243969 | 40 | 58 |
| yhfL | Bacillus subtilis | NP_388908 | 39 | 57 |
| Pfl-4354 | Pseudomonas fluorescens Pfo-1 | YP_350082 | 52 | 71 |
| EAV15023 | Comamonas testosterone KF-1 | ZP_01520072 | 55 | 72 |
| fadD1 | Pseudomonas aeruginosa | NP_251989 | 54 | 72 |
| fadD2 | Pseudomonas aeruginosa PAO1 | NP_251990 | 55 | 72 |
| fadD | Rhizobium etli CFN42 | YP_533919 | 55 | 72 |
| RPC_4074 | Rhodopseudomonas palustris Bis B18 | YP_533919 | 56 | 72 |
| fadD1 | Rasltonia Solanacearum GMI 1000 | NP_520978 | 56 | 72 |
| fadDD35 | Mycobacterium tuberculosis H37Rv | NP_217021 | 28 | 46 |
| fadDD22 | Mycobacterium tuberculosis H37Rv | NP_217464 | 23 | 42 |
| PRK0059 | Stenotrophomonas Maltophilia R551-3 | ZP_01644857 | 59 | 75 |

TABLE 1

Thioesterases

| Accession Number | Source Organism | Gene |
|---|---|---|
| AAC73596 | E. coli | tesA without leader sequence |
| AAC73555 | E. coli | tesB |
| Q41635, AAA34215 | Umbellularia california | fatB |
| AAC49269 | Cuphea hookeriana | fatB2 |
| Q39513; AAC72881 | Cuphea hookeriana | fatB3 |
| Q39473, AAC49151 | Cinnamonum camphorum | fatB |
| CAA85388 | Arabidopsis thaliana | fatB [M141T]* |
| NP 189147; NP 193041 | Arabidopsis thaliana | fatA |
| CAC39106 | Bradyrhiizobium japonicum | fatA |
| AAC72883 | Cuphea hookeriana | fatA |
| AAL79361 | Helianthus annus | fatA1 |

*Mayer et al., BMC Plant Biology 7: 1-11, 2007

The E. coli Acyl-CoA synthase (ACS) enzyme FadD and the fatty acid transport protein FadL are important components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which bind to the transcription factor FadR and derepress the expression of the fad genes that encode proteins responsible for fatty acid transport (FadL), activation (FadD), and β-oxidation (FadA, FadB, FadE, and FadH). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that will result in different end-products. See Caviglia et al., J. Biol. Chem. 279(12):1163-1169, 2004.

Production hosts can be engineered using known peptides to produce fatty acids of various lengths which can be converted to acyl-CoA. One method of making fatty acid derivatives involves increasing the expression of, or expressing more active forms of, one or more acyl-CoA synthase peptides (EC 6.2.1.-). A list of acyl-CoA synthases that can be expressed to produce acyl-CoA and fatty acid derivatives is shown in Table B.

Genes which encode ester synthases are known from the jojoba plant and the bacterium Acinetobacter sp. strain ADP 1 (formerly Acinetobacter calcoaceticus ADP 1). The bacterial ester synthase is a bifunctional enzyme, exhibiting ester synthase activity and the ability to form triacylglycerols from diacylglycerol substrates and fatty acyl-CoAs (acyl-CoA: diglycerol acyltransferase (DGAT) activity). The gene wax/dgat encodes both ester synthase and DGAT. See Cheng et al., J. Biol. Chem. 279(36):37798-37807, 2004; Kalscheuer and Steinbuchel, J. Biol. Chem. 278:8075-8082, 2003. Ester synthases may also be used to produce certain fatty esters which can be used as a fuel, such as biodiesel, as described herein. The production of fatty esters, including waxes, from acyl-CoA and alcohols, can be engineered using known polypeptides, such as one or more ester synthases (EC 2.3.1.20, 2.3.1.75). Ester synthase peptide sequences are publicly available, such as gene aft1, a bifunctional wax ester synthase/acyl-CoA:diacylglycerol acyltransferase (accession number AAO17391); and gene mWS, a wax ester synthase (simmondsia) (accession number AAD38041). Additionally, methods to identify ester synthase activity are provided in U.S. Pat. No. 7,118,896, which is herein incorporated by reference in its entirety.

In particular examples, if the desired product is an ester-based biofuel, the production host is modified so that it produces an ester generated from a crude carbon source. Such a production host includes an exogenous DNA sequence encoding an ester synthase that is expressed so as to confer upon said production host the ability to synthesize a saturated, unsaturated, or branched fatty ester from the crude carbon source. In some embodiments, the production host can also express DNA sequence encoding the following exemplary proteins: fatty acid elongases, acyl-CoA reductases, acyltransferases, ester synthases, fatty acyl transferases, diacylglycerol acyltransferases, acyl-coA wax alcohol acyltransferases. In an alternate embodiment, the organism expresses a DNA sequence encoding a bifunctional ester synthase/acyl-CoA:diacylglycerol acyltransferase. For example, the bifunctional ester synthase/acyl-CoA:diacylglycerol acyltransferase can be selected from the multienzyme complexes from *Simmondsia chinensis, Acinetobacter* sp. strain ADP1 (formerly *Acinetobacter calcoaceticus* ADP1), *Alcanivorax borkumensis, Pseudomonas aeruginosa, Fundibacter jadensis, Arabidopsis thaliana,* or *Alcaligenes eutrophus* (later renamed *Ralstonia eutropha*). In one embodiment, the fatty acid elongases, acyl-CoA reductases or wax synthases are from a multienzyme complex from *Alcaligenes eutrophus* (later renamed *Ralstonia eutropha*) or other organisms known in the literature to produce esters, such as wax or fatty esters.

Additional sources of heterologous DNA sequence encoding an ester synthase useful in fatty ester production include, but are not limited to, *Mortierella alpina* (e.g. ATCC 32222), *Cryptococcus curvatus* (also referred to as *Apiotricum curvatum*), *Alcanivorax jadensis* (for example T9T=DSM 12718=ATCC 700854), *Acinetobacter* sp. HO1-N, (e.g., ATCC 14987) and *Rhodococcus opacus* (e.g., PD630, DSMZ 44193).

In one example, the ester synthase from *Acinetobacter* sp. ADP1 at locus AAO17391 (described in Kalscheuer and Steinbuchel, *J. Biol. Chem.* 278:8075-8082, 2003, herein incorporated by reference) is used. In another example, the ester synthase from *Simmondsia chinensis* at locus AAD38041 is used.

An exemplary production host is LS9001. LS9001 was produced by modifying C41 (DE3), an *E. coli* B strain obtained from www.overexpress.com (Saint Beausine, France) to knock-out the fadE gene (acyl-CoA dehydrogenase). Briefly, the fadE knock-out strain of *E. coli* was made using primers YafV_NotI and Ivry_O1 to amplify about 830 bp upstream of fadE and primers Lpcaf_ol and LpcaR_Bam to amplify about 960 bp downstream of fadE. Overlap PCR was used to create a construct for in-frame deletion of the complete fadE gene. The fadE deletion construct was cloned into the temperature-sensitive plasmid pKOV3, which contained a sacB gene for counterselection, and a chromosomal deletion of fadE was made according to the method of Link et al., *J. Bact.* 179:6228-6237, 1997. The resulting strain was not capable of degrading fatty acids and fatty acyl-CoAs. This knock-out strain is herein designated as ΔfadE.

Additional modifications that were included in a production host include introducing a plasmid carrying the four genes which are responsible for acetyl-CoA carboxylase activity in *E. coli* (accA, accB, accC, and accD, Accessions: NP_414727, NP_417721, NP_417722, NP_416819, EC 6.4.1.2). The accABCD genes were cloned in two steps as bicistronic operons into the NcoI/HindIII and NdeI/AvrII sites of pACYCDuet-1 (Novagen, Madison, Wis.), and the resulting plasmid was termed pAS004.126.

Additional modifications that were included in a production host include the following: overexpression of aceEF (encoding the E1p dehydrogenase component and the E2p dihydrolipoamide acyltransferase component of the pyruvate and 2-oxoglutarate dehydrogenase complexes); and fabH/fabD/fabG/acpP/fabF (encoding FAS) from *E. coli, Nitrosomonas europaea* (ATCC 19718), *Bacillus subtilis, Saccharomyces cerevisiae, Streptomyces* spp, *Ralstonia, Rhodococcus, Corynebacteria, Brevibacteria, Mycobacteria,* and *oleaginous* yeast. Similarly, production hosts were engineered to express accABCD (encoding acetyl co-A carboxylase) from *Pisum savitum*. However, when the production host is also producing butanol it is less desirable to express the *Pisum savitum* homolog.

In some production hosts, genes were knocked out or attenuated using the method of Link, et al, *J. Bacteriol.* 179: 6228-6237, 1997. Genes that were knocked out or attenuated include gpsA (encoding biosynthetic sn-glycerol 3-phosphate dehydrogenase, accession NP_418065, EC: 1.1.1.94); ldhA (encoding lactate dehydrogenase, accession NP_415898, EC: 1.1.1.28); pflb (encoding formate acetyltransferase 1, accessions: P09373, EC: 2.3.1.54); adhE (encoding alcohol dehydrogenase, accessions: CAA47743, EC: 1.1.1.1, 1.2.1.10); pta (encoding phosphotransacetylase, accessions: NP_416800, EC: 2.3.1.8); poxB (encoding pyruvate oxidase, accessions: NP_415392 EC: 1.2.2.2); ackA (encoding acetate kinase, accessions: NP_416799, EC: 2.7.2.1) and combinations thereof.

Similarly, the PlsB[D311E] mutation was introduced into LS9001 to attenuate plsB. This mutation decreased the amount of carbon diverted to phospholipid production. An allele encoding PlsB[D311E] was made by replacing the GAC codon for aspartate 311 with a GAA codon for glutamate. The altered allele was made by gene synthesis and the chromosomal plsB wildtype allele was exchanged for the mutant plsB[D311E] allele using the method of Link et al.

An example of an engineered microbial cell is strain LS9-ID 1 MG1655 ΔfadE:: $P_{TRC}$-tesA-fadD-AtfAl1. This strain has four genetic modifications: knocked-out fadE, which eliminates the ability of the cell to utilize fatty acids as carbon source, and a chromosomal integration of an operon consisting of a modified intracellular thioesterase, an acyl-CoA synthase, and an ester synthase. These three enzymes confer the cells with the ability to produce and secrete fatty acid esters. Similar strains, except they also have additional knock-out and either native or heterologous genes expressed or overexpressed, allow for the production of other bioproducts of interest, for example, alkanes, olefins, ketones, and fatty alcohols.

Biomass/Crude Carbon Source

Starting with a biomass (or feedstock), preferably a renewable biomass, a carbon source for microbial cultures can be generated. The methods provided herein allows utilization of a crude carbon source, for example a processed biomass with high levels of toxins (relative to sugars), to be utilized for bioconversion to a bioproduct. The crude carbon source can be added to a microbial culture in increments, or continuously, during the course of the bioconversion, and the toxins are substantially removed as the bioconversion proceeds. The carbon source (e.g. basic sugars) is largely converted to the desired product or bioproduct. The toxins are referred to herein as toxic side products. Methods are also provided herein to improve the efficiency of utilization of the crude carbon source by having a step where a hydrophobic solvent is added as an ingredient to the preparation of the fermentation broth (or bioconversion broth) so that the toxic side product can be extracted in situ, before same can contact the microbial organism. Such a treatment can also be performed prior to the bioconversion instead of during it, if desired.

Cellulosic and Hemicellulosic Materials

Lignocellulosic materials are a source of biomass, and can include wood, grass, forestry waste, and agricultural residues (e.g., corn stover, bagasse, straw, etc.). Lignocellulosic materials can be processed to produce a carbon source. For example, these materials can serve as a substrate for different bioconversions if the carbohydrate constituents can be inexpensively depolymerized into soluble and fermentable sugars. The composition of the lignocellulosic materials is highly dependent on the source of the biomass, but all are composed of hemicelluloses, cellulose, and lignin. Hemicelluloses are branched polysaccharides of pentoses, hexoses, and uronic acids with different acetylation levels; cellulose is a high molecular weight linear polymer of D-glucose; lignin is an aromatic polymer of phenolic compounds. Both carbohydrate polymers can be hydrolyzed by mineral acids or enzymes, and most processes employ dilute acid hydrolysis of the hemicelluloses as an initial step to produce soluble sugars and increase the digestibility of cellulose with enzymes.

During dilute acid hydrolysis a complex mixture of microbial toxins is generated. These toxins include acetate from the deacetylation of xylan, furan degradation products (e.g., furfural and 5-hydroxymethyl furfural), aliphatic acids from sugars (e.g., formic and levulinic acid), and several phenolic compounds from lignin. No single compound has been identified as the dominant toxin, but furfural and its derivatives have been most often cited. Some compounds found in hydrolysates that have also been reported as microbial toxins include: 4-hydroxybenzaldehyde, 4-hydroxybenzoic acid, hydroquinone (1,4-di-hydroxybenzene), catechol (1,2-di-hydroxybenzene), syringaldehyde and syringic acid, from the degradation of syringyl propane units, and vanillic acid and vanillin derived from the degradation of the guaiacylpropane units of lignin.

Different modes of action on the microorganisms have been reported for the different type of toxins. For *E. coli* in particular, but also for a large number of other microorganism, Zaldivar et. al. (Biotech. Bioeng. Vol. 65, 1, 24-33, 1999) have reported that the potency of several toxins increase with their respective hydrophobicity as well as their chemical reactivity, The inhibitory concentration of the toxins is different for different organisms, and it also varies with environmental conditions, which can either potentiate or alleviate their effects. The present application is preferably useful for the hydrophobic toxins which will partition preferentially into the hydrophobic bioproducts or solvents of interest (e.g., fatty acids, fatty alcohols, fatty acid esters, alkanes, alkenes, etc.).

The concentration of the mentioned toxins in the biomass hydrolysates depends on the type of biomass as well as the conditions of the treatment. In general, values for total furans below 1.5 g/L have been cited, with furfural as the main component. Values for total phenolics compounds are in the order of a few hundred mg/L, with the total for each main group (hydroxyl-phenyl monomers, guaiacyl monomers and syringyl monomers) at no more than 100-200 mg/L. The concentrations used in the examples presented herein were much higher to clearly demonstrate that the benefits from the described treatments could extend towards much higher concentrations than those of normal hydrolysates. A fed-batch bioconversion process with described engineered microbial cells can allow for the collection and concentration of toxins over the duration of the fed-batch process. However, the present methods allow for removal of such toxins from the cell-contained aqueous layer and, therefore, reduce any inhibitory or deleterious affect of the toxins.

Fermentation

The methods described herein utilize some basic concepts of fermentation, and to that extent can incorporate known materials and methods available in the art for fermentation, particularly large-scale fermentation.

With the instant methods, engineered microbial cells can be cultured in a fermentor in the presence of a fermentation broth. Any suitable fermentor may be used including a stirred tank fermentor, an airlift fermentor, a bubble fermentor, or any combination thereof. Materials and Methods for the maintenance and growth of microbial cultures are well known to those in the art of microbiology or fermentation science (See for example, Bailey et. al., Biochemical Engineering Fundamentals, second edition, McGraw Hill, New York, 1986). Consideration must be given to appropriate growth medium, pH, temperature, and requirements for aerobic, microaerobic, or anaerobic conditions, depending on the specific requirements of the microorganism, the fermentation, and the process. The broth used is not critical, but it must support growth of the cell used and promote the enzymatic pathway necessary to produce the desired product. Exemplary broths can include minimal media, complex media, or defined media. The broth typically includes a fermentable carbon source, a nitrogen source (e.g., ammonium salt, yeast extract or peptone), minerals, salts, cofactors, buffers, and other components known to those skilled in the art The production and isolation of compounds can be enhanced by employing specific fermentation techniques. One method for maximizing production while reducing costs is increasing the percentage of the carbon from the carbon source that is converted to bioproducts. During normal cellular lifecycles, carbon is used in cellular functions including, for example, producing lipids, saccharides, proteins, organic acids, and nucleic acids. Reducing the amount of carbon necessary for growth-related activities can increase the efficiency of carbon bioconversion to bioproduct. This can be achieved by first growing microorganisms to a desired density, such as a density achieved at the peak of the log phase of growth. At such a point, replication checkpoint genes can be harnessed to stop the growth of cells.

The percentage of input carbons converted to bioproducts is a key cost driver—the more efficient (i.e., the higher the percentage of conversion) the less expensive the process. For oxygen-containing carbon sources (e.g., glucose or other carbohydrates), the oxygen must be released in the form of carbon dioxide. For every 2 oxygen atoms released, a carbon atom is also released leading to a maximal theoretical metabolic efficiency of about 34% (w/w) (for fatty acid derived products). This figure, however, changes for other bioproducts and carbon sources. Typical efficiencies in the literature are less than about 5%. Engineered cells that produce bioproducts can have greater than about 1, 3, 5, 10, 15, 20, 25, or 30% efficiency. In one example, cells will exhibit an efficiency of about 10% to about 25%. In other examples, such cells will exhibit an efficiency of about 25% to about 30%, and in other examples such cells will exhibit about 30% or higher efficiency.

In some examples, a continuous process can be employed. In this approach, a reactor with engineered microbial cells producing bioproducts can be assembled in multiple ways. In one example, the fermentation broth is continuously supplied to the fermentor and residual fermentation broth, engineered microbial cells, bioproduct, and side products are continuously removed from the fermentor. In an alternate embodiment, the removed cells can be separated and recycled back into the fermentor. In a further embodiment, some or all of the bioproduct is removed and recycled back into the fermentor to remove hydrophobic toxins from the newly introduced crude carbon source contained in the newly added fermentation broth.

In one example, the bioconversion will be undergoing a continuous reduction. In this instance, a stable reductive environment should be created. The reductive environment can be created by conducting the bioconversion in an anaerobic environment. The electron balance may be maintained by the release of carbon dioxide gas. Alternatively, nitrates or succinates can be provided in the broth to act as electron donors for the bioconversion in the absence of oxygen.

Efforts to augment the NAD(H) and NADP(H) balance can also facilitate stabilizing the electron balance. The availability of intracellular NADPH can also be enhanced by engineering the production host to express an NADH:NADPH transhydrogenase. The expression of one or more NADH:NADPH transhydrogenases converts the NADH produced in glycolysis to NADPH which enhances the production of fatty acid derivatives.

Production hosts or microbial cells (that are to be engineered) can be chosen for their endogenous ability to release hydrocarbons or bioproducts. The efficiency of bioproduct production and release into the broth can be expressed as a ratio of intracellular bioproduct to extracellular bioproduct. In some examples the ratio can be about 5:1, 4:1, 3:1, 2:1, 1:1, 1:2, 1:3, 1:4, or 1:5. The production host can be additionally engineered to express recombinant cellulosomes, which will allow the production host to use cellulosic material as a carbon source. Alternatively, the production host can be additionally engineered to express invertases (EC 3.2.1.26) so that sucrose can be used as a carbon source. Similarly, the production host can be engineered using the teachings described in one or more of U.S. Pat. Nos. 5,000,000, 5,028,539, 5,424,202, 5,482,846, and 5,602,030 (Ingram et al.), all of which are hereby incorporated by reference in their entirety, so that the production host can assimilate carbon efficiently and use cellulosic materials as carbons sources.

An important consideration for the fermentation process, or bioprocessing, is whether to use a batch or continuous fermentation process. One difference between the two processes that will influence the amount of bioproduct produced is the presence of a preparation, lag, and stationary phase for the batch process in addition to the exponential growth phase. In contrast, continuous processes are kept in a state of constant exponential growth and, if properly operated, can run for many months at a time. For bioproduct formation, continuous processes provide much higher productivities (i.e., dilution rate times cell mass) due to the elimination of the preparation, lag, and stationary phases. For example, increased productivity from a continuous process has been estimated at 8-fold (Shuler et al., Prentice Hall, Inc.: Upper Saddle River, N.J., 245-247).

Despite the overwhelming advantage in productivity, many more batch processes are in operation than continuous processes for a number of reasons. First, the productivity of a batch system may significantly exceed that of a continuous process because the latter would have to operate at very low dilution rates, which cannot easily be obtained when the process relies on processed biomass due to the resulting toxins present in the broth. Next, production strains generally have undergone modifications to their genetic material to improve their biochemical or protein production capabilities. These specialized strains are likely to grow less rapidly than their parental complements whereas continuous processes, such as those employing chemostats (fermentors operated in continuous mode), impose large selection pressures for the fastest growing cells. Cells containing recombinant DNA or carrying point mutations leading to the desired overproduction phenotype are susceptible to mutation back into the original, less productive, parental strain. It is also possible for strains having single gene deletions to develop compensatory mutations that will tend to restore the wild-type growth phenotype. The faster growing cells usually out-compete their more productive counterparts for limiting nutrients which can drastically reduce productivity. Batch processes, on the other hand, limit the number of generations available by not reusing cells at the end of each cycle, thus decreasing the probability of the production strain reverting back to its wild-type phenotype. Finally, continuous processes are more difficult to operate long-term due to the potential engineering obstacles, such as equipment failure and foreign organism contamination. The consequences of such failures are also much more considerable for a continuous process than for a batch process.

For small-volume production of compounds, the productivity increases of continuous processes rarely outweigh the risks associated with strain stability and reliability. However, for large volume production, the increases in productivity for a continuous process can result in significant economic gains when compared to a batch process. Although the engineering obstacles associated with continuous bioprocess operation are always present, the strain stability concerns can be overcome through metabolic engineering strategies that reroute molecular pathways to reduce or avoid negative selective pressures and favor production of the desired bioproduct during the exponential growth phase.

Biphasic Fermentation Process

One aspect of the invention comprises methods of improving production of a bioproduct from engineered microbial cells, comprising providing a fermentation broth comprising a crude carbon source; inoculating said fermentation broth with said microbial cells; and incubating the inoculated fermentation broth; wherein said bioproduct is a hydrophobic solvent immiscible with said fermentation broth, and wherein a toxic side product present in said crude carbon source is soluble in said hydrophobic solvent.

Another aspect of the invention comprises methods of passively phase-separating a toxic side product from an aqueous phase of a fermentation broth that is a mix of crude carbon source and microbial cells engineered to produce a bioproduct during fermentation of a culture of said microbial cells, comprising: providing a fermentation broth comprising a crude carbon source; inoculating said fermentation broth with said microbial cells to form a fermentation culture; and incubating said fermentation culture to yield production of said bioproduct; wherein said bioproduct is a hydrophobic solvent, and wherein a toxic side product present in said crude carbon source is soluble in said hydrophobic solvent.

Another aspect of the invention comprises kits for producing bioproducts from bioengineered cells, comprising: a sample of bioengineered cells that are bioengineered to produce a bioproduct from a carbon source; a fermentation broth comprising a crude carbon source derived from conversion of a biomass; a hydrophobic solvent immiscible with said fermentation broth and capable of extracting a toxic side product formed during conversion of said biomass; and instructions for a fermentation process using said sample of bioengineered cells, fermentation broth, and hydrophobic solvent.

Still another aspect of the invention comprises continuous fermentation processes for the production of a bioproduct from engineered microbial cells, comprising: providing a culture of said microbial cells; introducing a continuous flow of volume of a fermentation broth comprising a crude carbon source to said culture; fermenting said culture with said fermentation broth; and removing a continuous flow of volume of said fermentation broth from said culture; wherein said bioproduct is a hydrophobic solvent that is immiscible with said fermentation broth, and wherein toxic side product present in said crude carbon source is soluble in said hydrophobic solvent.

In still another aspect of the invention, provided are bioproducts produced by an engineered microbial cell by a process comprising: preparing a fermentation broth comprising a crude carbon source; inoculating said fermentation broth with said microbial cells; incubating the inoculated fermentation broth; recovering said bioproduct from the incubated fermentation broth; wherein said bioproduct is a hydrophobic solvent immiscible with said fermentation broth, and wherein toxic side product present in said crude carbon source is soluble in said hydrophobic solvent.

In yet another aspect of the invention, provided are vehicles powered by energy from combustion of a bioproduct produced by an engineered microbial cell by a process comprising: preparing a fermentation broth comprising a crude carbon source; inoculating said fermentation broth with said microbial cells; incubating the inoculated fermentation broth; recovering said bioproduct from the incubated fermentation broth; wherein said bioproduct is a hydrophobic solvent immiscible with said fermentation broth, and wherein toxic side product present in said crude carbon source is soluble in said hydrophobic solvent.

In some embodiments, the methods also include a step of pretreating said fermentation broth with an initial volume of a hydrophobic solvent; and removing said fermentation broth apart from said hydrophobic solvent. In some embodiments, the initial volume of hydrophobic solvent is mixed with said fermentation broth at a ratio of at most about 1:1 (volume: volume) hydrophobic solvent:fermentation broth; from about 1:1 to about 1:10,000; from about 1:1 to about 1:1,000; from about 1:1 to about 1:100; from about 1:3 to about 1:10,000; from about 1:3 to about 1:1,000; from about 1:3 to about 1:100; from about 1:10 to about 1:10,000; from about 1:10 to about 1:1,000; from about 1:10 to about 1:100; from about 1:100 to about 1:10,000; from about 1:100 to about 1:1,000; from about 1:100 to about 1:9,000; from about 1:100 to about 1:8,000; from about 1:100 to about 1:7,000; from about 1:100 to about 1:6,000; from about 1:100 to about 1:5,000; from about 1:100 to about 1:4,000; from about 1:100 to about 1:3,000; or from about 1:100 to about 1:2,000. Preferably, the vol:vol ratio is from about 1:3 to about 1:100 hydrophobic solvent:fermentation broth. One of ordinary skill can use routine skills to determine the best ratio to provide enough hydrophobic solvent to allow for effective solubilization of toxic side products into the hydrophobic solvent.

The crude carbon source is selected from those that are known to include or have impurities that are toxic side products. Preferably, the toxic side products are organic side products like those produced during the conversion of biomass (e.g., cellulosic material). In some embodiments, the toxic side products comprise furfural, 5-hydroxymethyl furfural, aliphatic acids, phenolic compounds, 4-hydroxybenzaldehyde, 4-hydroxybenzoic acid, hydroquinone, catechol, 4-methyl catechol, syringaldehyde, syringic acid, guaiacol, vanillic acid, or vanillin. Preferably, the toxic side products include furfural or furfural derivatives, such as 5-hydroxymethyl furfural. The hydrophobic solvent is a solvent chosen for its hydrophobic properties that allow for phase separation from the bioconversion broth, which is aqueous. One of ordinary skill, using routine skills, can readily pick out the hydrophobic solvent for use with the provided methods to allow for phase separation. In some embodiments, the hydrophobic solvent comprises alkanes, esters, olefins, fatty acids, fatty alcohols, aldehydes, or ketones. In some embodiments, the hydrophobic solvent comprises hexadecane, eicosadecene, C1C12:0 ester, C1C12:1 ester, C1C14:0 ester, C1C14:1 ester, C1C16:0 ester, C1C16:1 ester, C1C18:1 ester, C2C12:0 ester, C2C12:1 ester, C2C14:0 ester, C2:C14:1 ester, C2C16:0 ester, C2C16:1 ester, C2:C18:1 ester, or commercial biodiesel. In some embodiments, the hydrophobic solvent can be the same chemical as the bioproduct produced by the cells.

In one preferred example, the crude carbon source can be molasses. Tests for extractive fermentation or biphasic fermentation can be performed, as provided hereinafter. A stream of molasses at a flowrate of 10,000 kg/hr can be contacted with FAME at a flowrate of 10,000 kg/hour. Impurities are present in the molasses stream at a model concentration of 50.5 ppm each. If over 10% of a species is extracted, the specie may be considered to be partially hydrophobic or hydrophobic. These species are representative of typical chemistries of sugar cane or beet juice degradation products found in molasses. Some illustrative examples of hydrophobic species include: 1-acetyl-9H-pyrido[3,4B]indole; 1-acetylpyrrolidine; 2,3-dihydrobenzofuran; 2,5-dimethyl-4-hydroxy-3(2H)-furnine; 2,5-dimethylpyrazine; 2-hydroxy-3-methyl-2-cyclopenten-1-one; 5,6-dihydro-6-pentyl-2H-pyran-4-one; benzeneacetic acid; benzoic acid; furan carboxylic acid methylethylester; hexadecanoic acid; hexanoic acid; pentanoic acid; trimethylpyrazine; furfural; furan; n-hexanoic-acid; and 4-carboxybenzaldehyde.

The bioproducts discussed herein, which are produced by the provided engineered microbial cells, are biologically derived products that have commercial value as either end products or as intermediates (or reagents for further processing). The bioproducts provided herein have hydrophobic properties and can act as a hydrophobic solvent. The bioproducts can include products such as biofuels, polymers, organic reagents, and other industrial chemicals. In some embodiments, the bioproduct comprises alkanes, esters, olefins, fatty acids, fatty alcohols, aldehydes, or ketones. Preferably, the bioproduct is a biofuel.

The biomass provided herein is starting material for production of a carbon source, which often times requires a processing or converting step in order to breakdown the biomass into a useable carbon source, such as carbohydrate or sugar molecules, for utilization by the engineered microbial cells, which without further purification remains in a raw or processed state (the crude carbon source). Preferably, the biomass comprises molasses, hydrolyzed cellulosic, or hydrolyzed hemicellulosic material. In some embodiments, the cellulosic or hemicellulosic material comprises wood, grass, forestry waste, or agricultural residue (e.g., corn stover, bagasse, straw, etc.).

In some embodiments, the bioconversion processes provided can also include steps for diluting the broth used for bioconversion to reduce the concentration of the toxins. In one example, the broth can be diluted 5 fold or more.

Fuel Compositions

The biofuels provided herein, which are produced by the disclosed methods, can be optimized to provide a large-scale and commercially viable process for generating biofuels. Preferably, the process is cost-efficient and environmentally friendly. In one embodiment, the biofuels can provide a renewable source of energy for diesel machinery, including cars and planes. The biofuels can be used as an energy source either as a bulk fuel or as a component or additive to other available fuel sources.

Vehicles

The vehicles provided herein, are those that are manufactured for the purpose of use with biofuels and those that are retrofitted to effectively utilize biofuels. The vehicles can be powered by energy from combustion of the biofuel produced by an engineered microbial cell. Preferably, the biofuel is produced by the engineered microbial cell directly from a crude carbon source.

EXAMPLES

The present invention is further illustrated in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The following examples include fermentation processes, and the products generated therefrom, for the production of hydrophobic compounds such as biodiesel (ethyl and methyl esters of medium and long chain fatty acids), fatty alcohols, olefins and alkanes, using genetically engineered microorganisms. In general, the processes utilize carbohydrates as raw materials. Such materials can come from many different biomaterial sources, including for example corn, sugar cane, or hydrolysates of plant biomass. Preferably, the fermentation process consists of biomass pretreatments based on the fermentation product. Also, preferably, the fermentation process consists of the use of biphasic fermentations with the fermentation product acting as an extractant Example 1

Method of Fermenting Sugars to Produce Biodiesel

A culture of a genetically engineered strain of E. coli, LS9-ID1, was transferred from a frozen stock and incubated in Luria-Bertani broth for approximately three hours. The culture was transferred to a defined mineral medium commonly used for E. coli, M9, buffered and supplemented with thiamine and trace minerals. The culture was further incubated and used to inoculate the same fermentation media with 50 g/L of carbohydrate (glucose, fructose, some pentoses).

After initial growth the culture was induced with IPTG, and 10 ml/L of methanol or ethanol were added to start production of the biodiesel. Glucose was usually exhausted in 24-40 hours, and biodiesel production reached its peak similarly. The progression of the fermentation was followed by measurements of OD600 (optical density at 600 nm), glucose consumption and ester production. This protocol can be performed in shake flasks or in fermentors.

Glucose consumption throughout the fermentation was analyzed by High Pressure Liquid Chromatography (HPLC). The HPLC analysis was performed according to methods commonly used for some sugars and organic acids in the art, which includes the following conditions: Agilent HPLC 1200 Series with Refractive Index detector; Column: Aminex HPX-87H, 300 mm×7.8 mm; column temperature: 35° C.; mobile phase: 0.01M $H_2SO_4$ (aqueous); flow rate: 0.6 mL/min; injection volume: 20 µL.

The production of fatty acid methyl and ethyl esters was analyzed by gas chromatography with flame ionization detector (GC-FID). The samples from fermentation broth were extracted with ethyl acetate in a ratio of 1:1 vol/vol. After strong vortexing, the samples were centrifuged and the organic phase was analyzed by gas chromatography (GC). The analysis conditions were as follows: instrument: Trace GC Ultra, Thermo Electron Corporation with Flame ionization detector (FID) detector; column: DB-1 (1% diphenyl siloxane; 99% dimethyl siloxane) CO1 UFM 1/0.1/5 01 DET from Thermo Electron Corporation, phase pH 5, FT: 0.4 µm, length 5 m, id: 0.1 mm; inlet conditions: 250° C. splitless, 3.8 min 1/25 split method used depending upon sample concentration with split flow of 75 ml/min; carrier gas, flow rate: Helium, 3.0 ml/min; block temperature: 330° C.; oven temperature: 0.5 minute hold at 50° C.; 100° C./minute to 330° C., 0.5 minute hold at 330° C.; detector temperature: 300° C.; injection volume: 2 µL; run time/flow rate: 6.3 min/3.0 ml/min (splitless method), 3.8 min/1.5 ml/min (split 1/25 method), 3.04 min/1.2 ml/min (split 1/50 method).

Example 2

Determination of the Effect of Common Toxins on the Growth of the Production Strain The toxicity towards microbial strains of many of the compounds in hemicelluloses and cellulose hydrolysates has been examined individually. In the case of E. coli, the toxicity is related to the hydrophobicity of the toxin. The effects of several of these compounds on the growth of certain microbial strains were evaluated. The tests were done in shake flasks by following a protocol similar to that described in example 1, above, but without the induction and the addition of alcohols.

The toxins were added at the MIC (minimal inhibitory concentration that completely inhibits growth) as reported in the literature and cell growth was followed by OD measurements. Other concentrations were also tested to determine the range where the effect was observed. The results are presented in Table 1 and Table 2. The inhibition level was reported as the ratio between growth in the absence of the toxin (control) minus growth in the presence of the toxin and growth in the control.

TABLE 1

| Toxin | Reported MIC (g/L) | % Inhibition for LS9-ID1 |
| --- | --- | --- |
| Control | 0 | 0 |
| Furfural | 3.5 | 100 |
| Syringaldehyde | 2.5 | 100 |
| 4-hydroxybenzaldehyde | 1.25 | 100 |
| 5-Hydroxymethylfurfural | 4.0 | 100 |
| 4-Methyl catechol | 1.5 | 25 |
| Guaiacol | 3.0 | 100 |

TABLE 2

| Concentration | % of Growth inhibition | |
| --- | --- | --- |
| g/L | Furfural | Guaiacol |
| 1.00 | 0 | 0 |
| 1.50 | 60.0 | 41.7 |
| 2.00 | | 83.3 |
| 3.00 | 18.5 | 100 |

Example 3

Extractive Fermentations

To determine the ability to perform extractive fermentations using products generated by the engineered strain of E. coli, LS9-ID1, to improve the performance of the fermentation in the presence of toxins, the fermentations were performed using a protocol similar to that described in example 1, above. Two sets of duplicate flasks were prepared with different concentrations of the toxin to be tested. One set served as the control, which included the toxin without the extractant, the hydrophobic solvent. In the second set, the extractant was added in a ratio of 1 volume of solvent per 3 volumes of fermentation broth. The flasks were then inoculated and incubated at 37° C. in agitated shakers. When the OD 600 reached a value of 1, the cultures were induced by the addition of 1 mM IPTG and 20 ml/L methanol. Cell growth and production of fatty acids methyl esters (FAME) was measured at 24 hours. In cultures without hydrophobic solvents (control), OD was measured directly in the fermentation broth. In flasks with solvent there was interference in OD measurement, and to eliminate this problem, the broth was centrifuged and the cell pellet was resuspended in the same volume of distilled water. The OD was measured in this suspension.

To analyze FAME production, 0.5 ml of broth was well mixed with 0.5 ml of ethylacetate. The organic phase was analyzed by gas chromatography. In the samples with solvents, additional dilutions were applied. All the toxins were tested with ethyl oleate (C2:C18 ester, or C2:C18) as a solvent representative of a biodiesel. The results obtained for each toxin are shown in Tables 3 to 7. Growth and FAME production are reported as percentage of the control condition (no toxin added). Each result is the average of duplicate experiments.

TABLE 3

Furfural

| FURFURAL | % Growth | | % FAME titer | |
|---|---|---|---|---|
| Concentration (g/L) | No solvent | With C2:C18 | No solvent | With C2:C18 |
| 0.0 | 100.0 | 100.0 | 100.0 | 100.0 |
| 1.5 | 40.0 | 71.9 | 35.5 | 72.7 |
| 3.0 | 21.5 | 53.6 | 4.5 | 43.2 |

TABLE 4

Syringealdehyde

| SYRINGEALDEHYDE | % Growth | | % FAME titer | |
|---|---|---|---|---|
| Concentration (g/L) | No solvent | With C2:C18 | No solvent | With C2:C18 |
| 0.0 | 100.0 | 100.0 | 100.0 | 100.0 |
| 1.5 | 34.4 | 41.0 | 16.2 | 94.8 |
| 3.0 | 6.6 | 14.8 | 2.0 | 92.7 |

TABLE 5

4-Hydroxybenzaldehyde

| 4-HYDROXYBENZALDEHYDE | % Growth | | % FAME titer | |
|---|---|---|---|---|
| Concentration (g/L) | No solvent | With C2:C18 | No solvent | With C2:C18 |
| 0.00 | 100.0 | 100.0 | 100.0 | 100.0 |
| 0.63 | 70.0 | 68.0 | 54.3 | 72.6 |
| 1.25 | 45.0 | 60.0 | 18.1 | 31.8 |

TABLE 6

5-hydroxymethylfurfural

| 5-HYDROXYMETHYLFURFURAL | % Growth | |
|---|---|---|
| Concentration (g/L) | No solvent | With C2:C18 |
| 0.0 | 100.0 | 100.0 |
| 4.0 | 4.7 | 20.9 |
| 8.0 | 2.2 | 9.1 |

TABLE 7

Guaiacol

| GUAIACOL | % Growth | | % FAME titer | |
|---|---|---|---|---|
| Concentration (g/L) | No solvent | With C2:C18 | No solvent | With C2:C18 |
| 0.0 | 100.0 | 100.0 | 100.0 | 100.0 |
| 1.5 | 30.4 | 93.7 | 10.2 | 100.5 |
| 3.0 | 12.5 | 65.1 | 2.3 | 76.2 |

Example 4

Test of Different Solvents

Similar tests as that shown in Example 3, above, were performed using other solvents that can also be produced by genetically engineered organisms. Benefits achieved in cell growth and product concentration is based upon the differences in partition of each toxin between solvent and fermentation broth.

The solvents methyl laureate (C1:C12 ester, or C1:C12), hexadecane (an alkane), eicosadecene (an alkene) and commercial biodiesel were tested. The results are shown in Tables 8 through 11.

TABLE 8

| | | % Growth | |
|---|---|---|---|
| Toxin | Concentration (g/L) | No solvent | With C1:C12 |
| Furfural | 3.0 | 6.1 | 16.7 |
| 4-hydroxybenzaldehyde | 1.5 | 20.2 | 33.0 |
| Guaiacol | 1.5 | 18.3 | 88.6 |

TABLE 9

| | | % Growth | |
|---|---|---|---|
| Toxin | Concentration (g/L) | No solvent | With Hexadecane |
| Furfural | 1.5 | 17.7 | 38.5 |
| 4-hydroxybenzaldehyde | 1.5 | 6.2 | 53.8 |
| Guaiacol | 1.5 | 12.7 | 41.8 |
| 5-hydroxymethylfurfural | 2.0 | 39.8 | 57.1 |
| syringaldehyde | 1.5 | 19.5 | 40.7 |

TABLE 10

| Toxin | Concentration (g/L) | % Growth No solvent | % Growth With Eicosadecene |
|---|---|---|---|
| Furfural | 1.5 | 33.3 | 56.7 |
| 4-hydroxybenzaldehyde | 1.5 | 9.6 | 11.2 |
| Guaiacol | 1.5 | 15.8 | 31.8 |
| 5-hydroxymethylfurfural | 2.0 | 51.8 | 55.3 |
| Syringaldehyde | 1.5 | 8.8 | 48.2 |

TABLE 11

| Toxin | Concentration (g/L) | % Growth No solvent | % Growth With Biodiesel |
|---|---|---|---|
| Furfural | 1.5 | 33.3 | 49.7 |
| Syringaldehyde | 1.5 | 8.8 | 39.2 |

Example 5

Separation of Extraction and Fermentation

The raw materials can be treated to remove the toxin prior to the fermentation. For this purpose it will be possible to use the bioproduct after the initial steps of purification (centrifugal separation for example) but prior to any polishing or finishing step. The sugar containing raw material can be placed in contact with the solvent in a batch or in a continuous counter current mode. After extraction, the raw material (aqueous phase) can be separated from the solvent by decantation or centrifugation.

This approach can be particularly useful to remove toxins that partition more efficiently into the organic solvent at conditions different from those needed during fermentation. For instance, the weak organic acids present in biomass hydrolysate (hydroxybenzoic, vanillic, syringic) partition better into the organic solvent when they are not ionized, at low pH. This low pH may not be favorable for the cells, so it is preferable to perform the removal of the toxin before fermentation. Biomass hydrolysates are usually acidic, so they can be pretreated without other adjustments.

Tests were performed similarly to that described in the above Examples. Fermentation media was prepared and spiked with the desired concentration of the toxin. Methyl laureate was used as a solvent representative of biodiesel. It was added to the fermentation media in a 1:3 vol:vol ratio. Solvent and broth were thoroughly mixed at 37° C. for 60 minutes. The aqueous layer was decanted in a separatory funnel and collected. The resulting media was then inoculated with LS9-ID1 and growth was compared against similar media containing the toxin but which had not been treated. The results are presented in Table 12.

TABLE 12

| Toxin | Concentration (g/L) | % Growth No solvent | % Growth With Pretreatment | % Growth With Co-treatment |
|---|---|---|---|---|
| Furfural | 1.5 | 33.3 | 69.6 | |
| Syringaldehyde | 1.5 | 8.8 | 83.3 | 61.2 |

What is claimed is:

1. A method of producing a bioproduct from engineered microbial cells, comprising:
    (a) providing an aqueous fermentation broth comprising a crude carbon source;
    (b) inoculating said fermentation broth with microbial cells, engineered to enhance expression of one or more of a gene encoding an enzyme selected from the group consisting of thioesterase, acyl-CoA synthase, and ester synthase, and wherein a gene encoding an acyl-CoA dehydrogenase is attenuated or absent in the engineered microbial cells;
    (c) incubating the inoculated fermentation broth;
    (d) thereby producing and secreting a bioproduct; and
    (e) treating said fermentation broth with a hydrophobic solvent wherein a toxic side product present in said crude carbon source is soluble in said hydrophobic solvent.

2. The method of claim 1, further comprising:
    pretreating said fermentation broth with an initial volume of a hydrophobic solvent; and
    separating said fermentation broth from said hydrophobic solvent.

3. The method of claim 2, wherein the pretreating step comprises:
    mixing said initial volume of hydrophobic solvent with said fermentation broth at a ratio of at most about 1:1 (volume:volume) hydrophobic solvent:fermentation broth.

4. The method of claim 2, wherein the pretreating step comprises:
    mixing said initial volume of hydrophobic solvent with said fermentation broth at a ratio of from about 1:3 to about 1:100 (volume:volume) hydrophobic solvent:fermentation broth.

5. The method of claim 1, wherein said toxic side product comprises at least one compound selected from the group consisting of furfural; 5-hydroxymethyl furfural; aliphatic acids; phenolic compounds; 4-hydroxybenzaldehyde; 4-hydroxybenzoic acid; hydroquinone; catechol; 4-methyl catechol; syringaldehyde; syringic acid; guaiacol; vanillic acid; vanillin; 1-acetyl-9H-pyrido[3,4B]indole; 1-acetylpyrrolidine; 2,3-dihydrobenzofuran; 2,5-dimethyl-4-hydroxy-3(2H)-furnine; 2,5-dimethylpyrazine; 2-hydroxy-3-methyl-2-cyclopenten-1-one; 5,6-dihydro-6-pentyl-2H-pyran-4-one; benzeneacetic acid; benzoic acid; furan carboxylic acid methylethylester; hexadecanoic acid; hexanoic acid; pentanoic acid; trimethylpyrazine; furan; n-hexanoic-acid; and 4-carboxybenzaldehyde.

6. The method of claim 1, wherein said hydrophobic solvent comprises alkanes, esters, olefins, fatty acids, fatty alcohols, aldehydes, or ketones.

7. The method of claim 6, wherein said hydrophobic solvent comprises hexadecane, eicosadecene, C1C12:0 ester, C1C12:1 ester, C1C14:0 ester, C1C14:1 ester, C1C16:0 ester, C1C16:1 ester, C1C18:1 ester, C2C12:0 ester, C2C12:1 ester, C2C14:0 ester, C2:C14:1 ester, C2C16:0 ester, C2C16:1 ester, C2:C18:1 ester, or biodiesel.

8. The method of claim 1, wherein said bioproduct comprises one or more of alkanes, esters, olefins, fatty acids, fatty alcohols, aldehydes, or ketones.

9. The method of claim 8, wherein said bioproduct comprises hexadecane, eicosadecene, C1C12:0 ester, C1C12:1 ester, C1C14:0 ester, C1C14:1 ester, C1C16:0 ester, C1C16:1 ester, C1C18:1 ester, C2C12:0 ester, C2C12:1 ester, C2C14:0 ester, C2:C14:1 ester, C2C16:0 ester, C2C16:1 ester, C2:C18:1 ester, or biodiesel.

10. The method of claim 1, wherein said bioproduct is a biofuel.

11. The method of claim 1, wherein said hydrophobic solvent and said bioproduct comprise similar molecules.

12. The method of claim 1, wherein said crude carbon source is derived from biomass.

13. The method of claim 12, wherein said crude carbon source comprises hydrolyzed cellulosic material, hydrolyzed hemicellulosic material, or molasses.

14. The method of claim 13, wherein said cellulosic or hemicellulosic material comprises wood, grass, forestry waste, agricultural residue, or agroindustrial residue.

15. A method of producing a bioproduct from engineered microbial cells, comprising:
 (a) providing an aqueous fermentation broth comprising a crude carbon source;
 (b) inoculating said fermentation broth with engineered microbial cells wherein the engineered microbial cells are engineered to enhance expression of a gene encoding an enzyme selected from the group consisting of thioesterase, acyl-CoA synthase, and ester synthase and wherein a gene encoding an acyl-CoA dehydrogenase is attenuated or absent in the engineered microbial cell; and
 (c) incubating the inoculated fermentation broth,
 wherein the engineered microbial cells produce a bioproduct and said bioproduct is a hydrophobic solvent immiscible with said fermentation broth, wherein any toxic side product present in said crude carbon source is soluble in a hydrophobic solvent.

16. The method of claim 15, wherein the gene encoding an acyl-CoA dehydrogenase is fadE.

* * * * *